United States Patent
Wu (10) Patent No.: US 7,235,567 B2
(45) Date of Patent: *Jun. 26, 2007

(54) CRYSTALLINE POLYMORPH OF A BISULFATE SALT OF A THROMBIN RECEPTOR ANTAGONIST

(75) Inventor: Wenxue Wu, Princeton Junction, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/755,066

(22) Filed: Jan. 9, 2004

(65) Prior Publication Data

US 2004/0176418 A1 Sep. 9, 2004

Related U.S. Application Data

(63) Continuation-in-part of application No. 10/705,282, filed on Nov. 10, 2003, which is a continuation-in-part of application No. 10/671,216, filed on Sep. 25, 2003, which is a continuation-in-part of application No. 09/880,222, filed on Jun. 13, 2001, now Pat. No. 6,645,987, which is a continuation-in-part of application No. 10/412,982, filed on Apr. 14, 2003.

(60) Provisional application No. 60/373,072, filed on Apr. 16, 2002, provisional application No. 60/211,724, filed on Jun. 15, 2000.

(51) Int. Cl.
  *A61K 31/4427* (2006.01)
  *C07D 405/02* (2006.01)
(52) U.S. Cl. ............... 514/337; 546/268.1; 546/276.7
(58) Field of Classification Search ............ 546/268.1, 546/276.7; 514/337
See application file for complete search history.

(56) References Cited

U.S. PATENT DOCUMENTS

| | | | |
|---|---|---|---|
| 6,645,987 B2 | 11/2003 | Chackalamannil et al. | |
| 6,894,065 B2 | 5/2005 | Chackalamannil et al. | |
| 2003/0203927 A1* | 10/2003 | Chackalamannil et al. | . 514/291 |
| 2003/0216437 A1* | 11/2003 | Chackalamannil et al. | . 514/333 |
| 2004/0192753 A1* | 9/2004 | Chackalamannil et al. | . 514/411 |

FOREIGN PATENT DOCUMENTS

| WO | WO/9926943 A | 6/1999 |
|---|---|---|
| WO | WO/0196330 A | 12/2001 |
| WO | WO 03/089428 A | 10/2003 |
| WO | WO 05/046688 A2 | 5/2005 |

OTHER PUBLICATIONS

Int'l Search Report for PCT/US2005/000447; May 11, 2005; 4 pages.
Hsieh, Y. et.al.; "Simultaneous determination of a drug candidate and its metabolite in rat plasma samples using ultrafast monolithic column high-performance liquid chromato-graphy/tandem mass spectrometry"; Rapid Comm. in Mass Spectometry;2002;16: 944-950.
Bernatowicz, M.; "Dev. of Potent Thrombin Receptor Antagonist peptides", J. Med. Chem.; 1996, 39, 4879-4887.

* cited by examiner

*Primary Examiner*—Rita Desai
(74) *Attorney, Agent, or Firm*—Gerard E. Reinhardt (57) ABSTRACT

A crystalline polymorph of a bisulfate salt of a thrombin receptor antagonist compound, which exhibits a powder x-ray diffraction profile substantially the same as that shown in FIG. 1, or which exhibits a differential scanning calorimtery profile substantially the same as that shown in FIG. 3, and is represented by the formula for Compound 2:

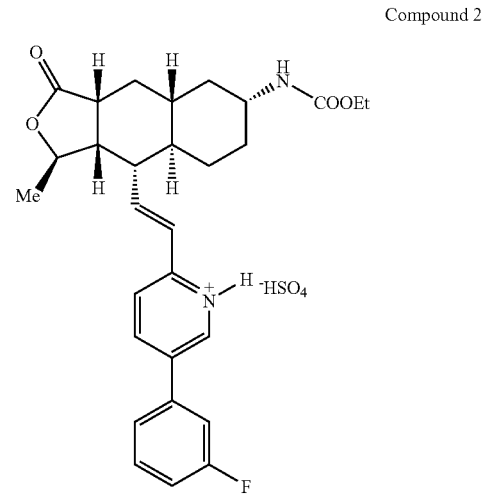

Compound 2 and processes for preparing Compound 2 are disclosed.

Pharmaceutical compositions comprising the polymorph of the bisulfate salt and at least one excipient or carrier, and methods of using the polymorph of Compound 2 to treat a variety of physiological disorders, such as thrombosis, are also disclosed.

7 Claims, 3 Drawing Sheets

CRYSTALLINE POLYMORPH OF A BISULFATE SALT OF A THROMBIN RECEPTOR ANTAGONIST

CROSS-REFERENCE TO RELATED APPLICATIONS

The present application is a Continuation-in-Part of: 1) a co-pending U.S. Continuation-in-Part application Ser. No. 10/705,282 filed Nov. 10, 2003; which is a Continuation-in-Part of U.S. application Ser. No. 10/671,216 filed Sep. 25, 2003, which is a Continuation in part of U.S. application Ser. No. 09/880,222 filed Jun. 13, 2001 now U.S. Pat. No. 6,645,987, which claims the benefit of U.S. Provisional Application No. 60/211,724 filed Jun. 15, 2000, and 2) is a Continuation in part of U.S. application Ser. No. 10/412,982 filed Apr. 14, 2003, which claims the benefit of U.S. Provisional Application No. 60/373,072, filed Apr. 16, 2002, the complete text and claims of which are incorporated by reference herein as if fully set forth.

BACKGROUND OF THE INVENTION

The invention relates to a crystalline polymorph of a bisulfate salt of a thrombin receptor antagonist, processes for synthesizing the bisulfate salt and methods of using the bisulfate salt.

BACKGROUND

Thrombin is known to have a variety of activities in different cell types and thrombin receptors are known to be present in such cell types as human platelets, vascular smooth muscle cells, endothelial cells and fibroblasts. It is therefore possible that thrombin receptor antagonists, also known as protease activated receptor (PAR) antagonists will be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, vol. 39, pp. 4879–4887 (1996), tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor antagonists are also disclosed in WO 94/03479, published Feb. 17, 1994.

Thrombin receptor antagonists have been suggested in the literature as being potentially useful in treating a variety of diseases or conditions including, for example, thrombosis, vascular restenosis, deep venous thrombosis, lung embolism, cerebral infarction, heart disease, disseminated intravascular coagulation syndrome, hypertension, inflammation, rheumatism, asthma, glomerulonephritis, osteoporosis, neuropathy and/or malignant tumors (Suzuki, Shuichi, PCT Int. Appls. WO 0288092 (2002), WO 0285850 (2002) and WO 0285855 (2002)), arrhythmia, inflammation, angina, stroke, atherosclerosis, ischemic conditions, angiogenesis related disorders, cancer, and neurodegenerative disorders (Zhang, Han-cheng, PCT Int. Appl. WO 0100659 (2001), WO 0100657(2001) and WO 0100656 (2001)), disorders of the liver, kidney and lung (Chambers, R. C., "Coagulation cascade proteases and tissue fibrosis," *Biochemical Society Transactions*, 2002, 30(2), pp. 194–200), cancer (Nguyen, Quang-De, "RhoA- and RhoD-dependent regulatory switch of Gα subunit signaling by PAR-1 receptors in cellular invasion," *FASEB Journal*, 2002, 16(6), pp. 565–576), melanoma (Tellez, Carmen, "Role and regulation of the thrombin receptor (PAR-1) in human melanoma," *Oncogene* 22, 2003, pp. 3130–3137), renal cell carcinoma (Kaufman, R., "Meizothrombin, an intermediate of prothrombin cleavage potently activates renal carcinoma cells by interaction with PAR-type thrombin receptors," *Oncology Reports*, 2003, 10(2), pp. 493–496), renal disease, acute renal failure, chronic renal failure, renal vascular homeostasis (Tognetto, Michele, "Proteinase-activated receptor-1 (PAR-1) activation contracts the isolated human renal artery in vitro," *British Journal of Pharmacology*, 2003, 139(1), pp. 21–27), glomerulonephritis (Ahn, Ho-Sam, "Nonpeptide thrombin receptor antagonists," *Drugs of the Future*, 2001, 26(11), pp. 1065–1085), inflammation, (Meli, Rosaria, "Thrombin and PAR-1 activating peptide increase iNOS expression in cytokine-stimulated C6 glioma cells," *Journal of Neurochemistry*, 2001, 79(3), pp. 556–563), chronic airways disease (Roche, Nicolas, "Effect of acute and chronic inflammatory stimuli on expression of protease-activated receptors 1 and 2 alveolar macrophages," *Journal of Allergy and Clinical Immunology*, 2003, 111(2), pp. 367–373), bladder inflammation (D'Andrea, Michael R., "Expression of protease-activated receptor-1, -2, -3 and 4 in control and experimentally inflamed mouse bladder," *American Journal of Pathology*, 2003, 162(3), pp. 907–923), neurodegenerative and/or neurotoxic diseases, conditions, and injuries (Traynelis, Stephen Francis, "Treatment of neurodegenerative diseases and conditions using PAR-1 antagonists," PCT Int. Appl. WO 0271847 (2002)), radiation fibrosis, endothelial dysfunction (Wang, Junru, "Deficiency of microvascular thrombomodulin and up-regulation of protease-activated receptor-1 in irradiated rat intestine: possible link between endothelial dysfunction and chronic radiation fibrosis," *American Journal of Pathology*, June 2002, 160(6), pp. 2063–72), periodontal diseases (Tanaka, Nobuhisa, "Thrombin-induced Ca$^2$+ mobilization in human gingival fibroblasts is mediated by protease-activated receptor-1 (PAR-1)," *Life Sciences*, 2003, 73, pp. 301–310) and wounds (Strukova, S. M., "Thrombin, a regulator of reparation processes in wound healing," *Bioorganicheskaya Khimiya*, 1998, 24(4), pp. 288–292).

Thrombin receptor antagonists have also been suggested as potential antiangiogenics (Chan, Barden, "Antiangiogenic property of human thrombin," *Microvascular Research*, 2003, 66(1), pp. 1–14), resistance factors for tumor cells towards chemotherapy (Schiller, H., "Thrombin as a survival factor for cancer cells: thrombin activation in malignant effusions in vivo and inhibition of idarubicin-induced cell death in vitro," *Int'l. J. of Clinical Pharmacology and Therapeutics*, 2002, 40(8), pp. 329–335.), platelet aggregation inhibitors and proliferation inhibitors of smooth muscle cells, endothelial cells, fibroblasts, kidney cells, osteosarcoma cells, muscle cells, cancer cells and/or glial cells (Suzuki, supra).

Substituted thrombin receptor antagonists are disclosed in U.S. Pat. Nos. 6,063,847, 6,326,380 and U.S. Ser. No. 10/271,715.

U.S. application Ser. No. 10/412,982, which is incorporated herein by reference in its entirety, teaches a class of thrombin receptor antagonist compounds having the formula (I) as follows:

and pharmaceutically acceptable salts and solvates thereof, wherein the substituents and structural features are as defined therein. A general process is also disclosed therein for preparing such thrombin receptor antagonist compounds.

U.S. application Ser. No. 10/412,982 further discloses a specific thrombin receptor antagonist compound identified as Example 2, herein identified as Compound 1. Compound 1 has the following structure:

Compound 1

Compound 1 exhibits good thrombin receptor antagonist activity (potency) and selectivity, and is useful for treating thrombosis, other cardiovascular and non-cardiovascular conditions. The co-pending U.S. patent application Ser. No. 10/705,282, herein incorporated by reference, discloses a variety of indications and combination formulations for thrombin receptor antagonists.

It would be beneficial to improve the thermodynamic properties of Compound 1. It would further be beneficial to produce a stable crystalline form of a compound related to Compound 1, which has consistent physical properties. The invention seeks to provide these and other benefits, which will become apparent as the description progresses.

SUMMARY OF THE INVENTION

The invention provides a crystalline polymorph Form 1 of Compound 2 of the formula:

that exhibits a powder x-ray diffraction pattern having characteristic peak locations of 11.2, 16.4, 19.2 and 21.0 degrees 2θ. More preferably, the crystalline polymorph exhibits a powder x-ray diffraction pattern having characteristic peak locations of 9.9, 11.2, 16.4, 19.2, 21.0, 22.1, 23.7 and 26.7 degrees 2θ. Even more preferably, the crystalline polymorph exhibits a powder x-ray diffraction pattern having characteristic peak locations of 9.9, 11.2, 12.6, 14.5, 16.4, 19.2, 21.0, 22.1, 23.7, 26.7, 28.2 and 30.8 degrees 2θ.

Figure 1:
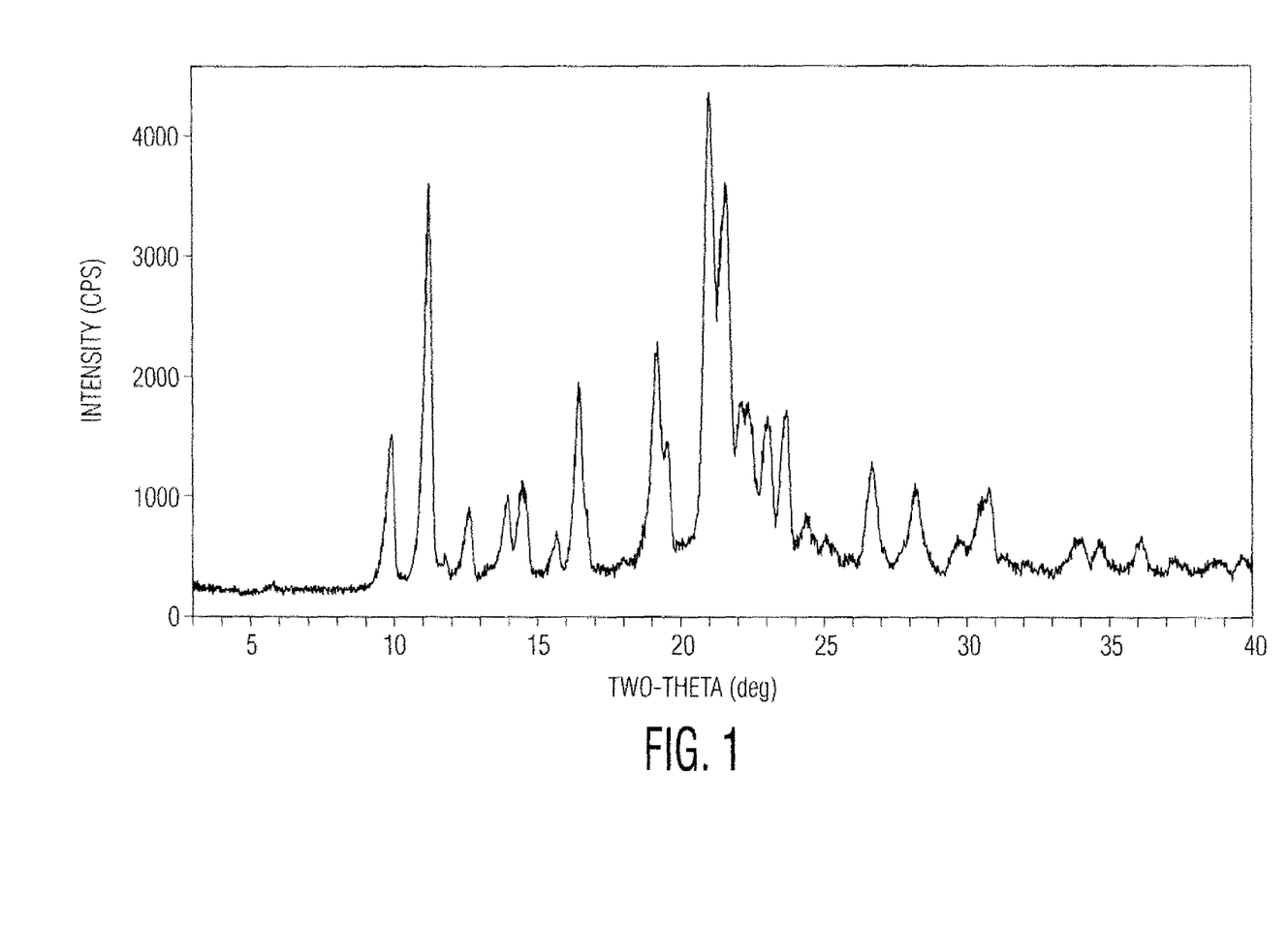
FIG. 1 is a graph of a powder x-ray diffraction (PXRD) pattern of Form 1 of Compound 2 crystallized from acetonitrile, generated using a Rigaku MiniFlex diffractometer. The graph plots the intensity of the peaks as defined by counts per second versus the diffraction angle 2θ in degrees.

In a further embodiment, the invention provides a crystalline polymorph Form 1 of Compound 2 that exhibits a powder x-ray diffraction pattern substantially the same as the powder x-ray diffraction pattern shown in FIG. 1.

Figure 3:
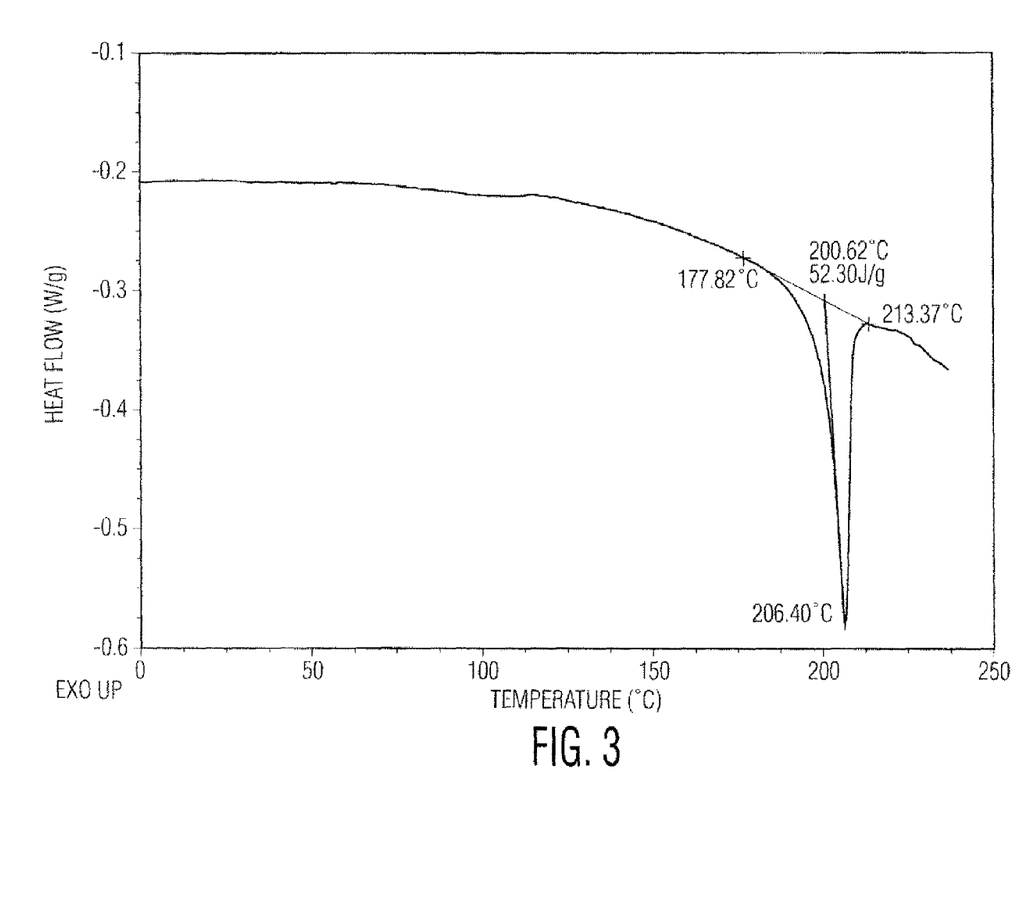
FIG. 3 is a graph of a modulated Differential Scanning Calorimetry (DSC) thermogram of Form 1 of Compound 2 crystallized from acetonitrile. The graph plots the normalized heat flow in units of Watts/gram ("W/g") versus the measured sample temperature in degrees C.

In a further embodiment, the invention provides a crystalline polymorph Form 1 of Compound 2 that exhibits a differential scanning calorimetry pattern substantially the same as the differential scanning calorimetry pattern shown in FIG. 3.

In further embodiments, the invention provides a process for preparing Compound 2 from Compound 1 according to the reaction:

-continued

2 comprising:
  a) mixing Compound 1 in an organic solvent to form a mixture;
  b) heating the mixture to a temperature of about 40–80° C.; and
  c) adding sulfuric acid to the heated mixture.

In yet further embodiments, the invention provides the crystalline polymorph Form 1 of Compound 2 that is the product of the above process.

Preferably, the organic solvent is selected from the group consisting of alcohol, nitrile, ester, ketone, ether and mixtures thereof. Even more preferably, the organic solvent is acetonitrile. Preferably, the sulfuric acid is in a mixture with acetonitrile. Preferably, the temperature is about 50° C.

In further embodiments, the invention provides a pharmaceutical composition comprising the crystalline polymorph Form 1 of Compound 2 and at least one excipient or carrier.

In yet further embodiments, the invention provides a method of inhibiting thrombin receptors comprising administering to a mammal in need of such treatment an effective amount of the crystalline polymorph Form 1 of Compound 2.

In still further embodiments, the invention provides a method of treating thrombosis, atherosclerosis, restenosis, hypertension, angina pectoris, arrhythmia, heart failure, myocardial infarction, glomerulonephritis, thrombotic stroke, thromboembolic stroke, peripheral vascular diseases, inflammatory disorders, cerebral ischemia or cancer, comprising administering to a mammal in need of such treatment an effective amount of the crystalline polymorph Form 1 of Compound 2.

In even further embodiments, the invention provides a method of treating thrombosis, atherosclerosis, restenosis, hypertension, angina pectoris, arrhythmia, heart failure, myocardial infarction, glomerulonephritis, thrombotic stroke, thromboembolytic stroke, peripheral vascular diseases, inflammatory disorders, cerebral ischemia or cancer, comprising administering to a mammal in need of such treatment an effective amount of the crystalline polymorph Form 1 of Compound 2 in combination with at least one additional cardiovascular agent. Preferably, the at least one additional cardiovascular agent is selected from the group consisting of thromboxane A2 biosynthesis inhibitors, GP IIb/IIIa antagonists, thromboxane antagonists, adenosine diphosphate inhibitors, cyclooxygenase inhibitors, angiotensin antagonists, endothelin antagonists, angiotensin converting enzyme inhibitors, neutral endopeptidase inhibitors, anticoagulants, diuretics, and platelet aggregation inhibitors. More preferably, the at least one additional cardiovascular agent is aspirin or clopidogrel bisulfate.

In even further embodiments, the invention provides a purified form of the crystalline polymorph Form 1 of Compound 2.

A further understanding of the invention will be had from the following drawings, description and claims.

DETAILED DESCRIPTION

As discussed in U.S. application Ser. No. 10/412,982, Compound 1 is a potent thrombin receptor antagonist.

I

However, the freebase form of Compound 1 was found to suffer from inferior crystalline stability. A bisulfate salt of Compound 1 was found to exhibit superior stability characteristics and substantially similar activity. As used herein, "bisulfate" means—$HSO_4$. Compound 2 has the following structure:

Compound 2

Two distinct crystalline polymorphs of Compound 2 were found to exist. These two forms are herein referred to as Form 1 and Form 2. Form 2 was found to be unstable, and to revert to the crystalline structure of Form 1 over time. The two crystalline forms of the bisulfate salt can be referred to as polymorphs.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

Compound 2 has at least one bond with restricted rotation. All tautomers and rotational isomers are contemplated as being part of the invention.

Compound 2 can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

As used throughout the specification, the following terms, unless otherwise indicated, shall be understood to have the following meanings:

"Patient" includes both human and other animals.

"Mammal" includes humans and other mammalian animals.

"Polymorph" means a crystalline form of a substance that is distinct from another crystalline form but that shares the same chemical formula.

"Alcohol" means an organic compound containing a hydroxyl group (—OH).

"Nitrile" means an organic compound containing a —C≡N group.

"Ester" means an organic compound of formula RC(O)OR, wherein the two R groups are independently alkyl or aryl and the parentheses indicate that the enclosed O is doublebonded to the C.

"Ketone" means an organic compound containing a carbonyl group (C=O) attached to two alkyl groups.

"Excipient" means an essentially inert substance used as a diluent or to give form or consistency to a formulation.

"Effective" or "therapeutically effective" is meant to describe a compound or a composition of the present invention effective in antagonism of thrombin receptors and thus producing the desired therapeutic, ameliorative, inhibitory or preventative effect. "Effective amount" or "therapeutically effective amount" is meant to describe an amount of compound or a composition of the present invention effective in antagonism of thrombin receptors and thus producing the desired therapeutic, ameliorative, inhibitory or preventative effect.

Sample Preparation

Form 1 of Compound 2 was analyzed as a dry powder for powder x-ray diffraction ("PXRD") and modulated Differential Scanning Calorimetry ("DSC") analyses. Prior to analysis, a micronizer was used to grind and classify the material. Filtered nitrogen was introduced through jets spaced at regular intervals around the periphery of the grinding chamber. During operation, a high-speed vortex is generated, and the material was injected into the vortex near the peripheral wall. Strong velocity gradients near the jets cause the suspended particles to collide and reduce one another by impact. Heavier oversized particles are held in the grinding area by centrifugal force. The rate of feed and the grinding gas pressure are the main factors that control the output particle size. The grinding gas exits through an outlet at the top center of the chamber and draws the micronized product with it into the collection bag. The batch was micronized at a feed rate of 150 grams per minute ("g/min") and a mill pressure of 50 psig on a 4 inch micronizer. The ground material was collected in drums lined with double-polyethylene bags and stored in a refrigerated area.

Following micronization, samples were analyzed with minimal preparation to prevent any form changes. The samples were lightly rubbed to insure that particles were not clumped together. No solvents, drying or other preparation steps were used for these analyses. The PXRD and DSC data can each uniquely identify the single form.

Powder X-Ray Diffraction

The PXRD analysis was performed using the Rigaku MiniFlex® diffractometer (manufactured in 1999). The instrument uses a variable divergence slit with a θ/2 θ scan axis configuration and a radiation source of copper (Kα). The polymorph sample was supplied in powder form and subsequently placed onto a face of a Si-coated low background scatter aluminum plate using a hand held dowel with a minimum of force. A crystalline silicon standard was used to check peak position accuracy. The sample was exposed to ambient conditions while being rotated at 54 revolutions per minute ("rpm") to reduce preferred orientations of the crystals. The data were evaluated using JADE® pattern processing software version 5.0 from Materials Data Inc. ("MDI"). The software automatically does a final filtering, fits a background, and measures the area and height of each peak. The x-ray pattern was filtered with a nine-point Savitzky-Golay parabolic filter, but otherwise it is essentially a raw pattern without a background correction or a K-α2 peak removal.

Using the methods and equipment described above, Form 1 of Compound 2 was subjected to PXRD analysis. A PXRD pattern was generated and is displayed in FIG. 1. The intensity of the peaks (y-axis is in counts per second) is plotted versus the 2θ angle (x-axis is in degrees 2θ). In addition, the data were plotted with detector counts normalized for the collection time per step versus the 2θ angle. Peak locations (on the 2θ X-axis) consistent with these profiles are displayed in Table 1. The locations of these PXRD peaks are characteristic of crystalline polymorph Form 1 of Compound 2.

TABLE 1

PXRD Peak Positions for Form 1 of Compound 2

| 2θ (°) |
| --- |
| 9.90 |
| 11.24 |
| 11.77 |
| 12.64 |
| 13.96 |
| 14.48 |
| 15.68 |
| 16.44 |
| 17.97 |
| 19.22 |
| 19.52 |
| 21.04 |
| 21.58 |
| 22.38 |
| 23.06 |
| 23.70 |
| 24.36 |
| 25.06 |
| 25.89 |
| 26.68 |
| 28.20 |
| 29.74 |
| 30.78 |
| 32.16 |
| 34.06 |
| 34.66 |
| 36.12 |
| 37.30 |

Starting with the PXRD peak locations of the Form 1 crystalline structure of Compound 2 as displayed in Table 1, the most characteristic peak locations can be selected and grouped by relative intensity to conveniently distinguish this crystalline structure from others. Such a selection of unique peaks is displayed in Table 2. Thus, the crystalline structure of Form 1 of Compound 2 may be identified by the Peak Location Group No. 1, consisting of 4 characteristic PXRD peak locations. More preferably, the crystalline structure of Form 1 of Compound 2 may be identified by the Peak Location Group No. 2, consisting of the 4 characteristic PXRD peak locations of Group No. 1 and an additional 4 peak locations. Still more preferably, the Form 1 crystalline structure of Compound 2 may be identified by the Peak Location Group No. 3, consisting of the 8 characteristic PXRD peak locations of Group No. 2 and an additional 4 peak locations.

TABLE 2

Characteristic PXRD Peak Locations for Form 1 of Compound 2

| Peak Location Group No. | Peak Location (degrees 2θ) |
| --- | --- |
| 1 | 11.2 |
|   | 16.4 |
|   | 19.2 |
|   | 21.0 |
| 2 | 9.9 |
|   | 11.2 |
|   | 16.4 |
|   | 19.2 |
|   | 21.0 |
|   | 22.1 |
|   | 23.7 |
|   | 26.7 |
| 3 | 9.9 |
|   | 11.2 |
|   | 12.6 |
|   | 14.5 |
|   | 16.4 |
|   | 19.2 |
|   | 21.0 |
|   | 22.1 |
|   | 23.7 |
|   | 26.7 |
|   | 28.2 |
|   | 30.8 |

Figure 2:
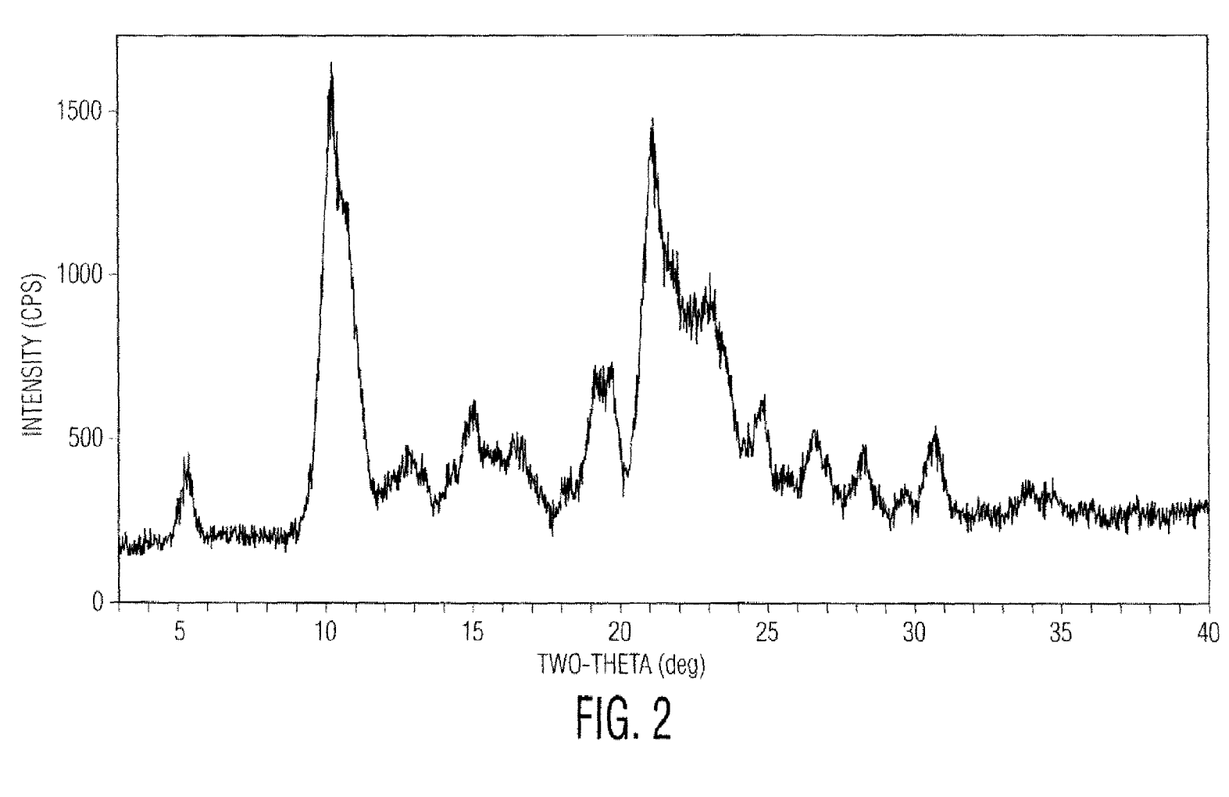
FIG. 2 is a graph of a powder x-ray diffraction (PXRD) pattern of Form 2 of Compound 2 synthesized from a slurry of the bisulfate salt in acetone at room temperature. The graph was generated using a Rigaku MiniFlex diffractometer. The graph plots the intensity of the peaks as defined by counts per second versus the diffraction angle 2 θ in degrees.

Form 2 of Compound 2 was also subject to PXRD analysis. The Form 2 crystals were synthesized from a slurry of the bisulfate salt in acetone at room temperature. The Form 2 crystals were not micronized. The crystal sample preparation, analytical equipment and analytical techniques used to analyze the crystalline structure of Form 2 were otherwise similar to those applied to Form 1, as described above. The PXRD profile of the Form 2 material is displayed in FIG. 2. The PXRD peak locations of the Form 2 crystalline structure of Compound 2 are displayed in Table 3. A comparison of the PXRD peak locations displayed in Tables 1 and 3 supports the conclusion that Forms 1 and 2 are distinct crystalline polymorphs of the bisulfate salt of Compound 2.

TABLE 3

PXRD Peak Positions for Form 2 of Compound 2

| 2θ Angle (°) |
| --- |
| 5.36 |
| 10.22 |
| 10.72 |
| 12.92 |
| 13.38 |
| 15.02 |
| 16.67 |
| 19.16 |
| 19.72 |
| 21.14 |
| 21.79 |
| 23.06 |
| 24.89 |
| 26.60 |
| 27.02 |
| 28.24 |
| 29.67 |
| 30.70 |
| 33.92 |
| 34.71 |

Those skilled in the art will recognize that the measurements of the PXRD peak locations for a given crystalline form of the same compound will vary within a margin of error. In U.S. application Ser. No. 10/449,650, the maximum sample-to-sample 2-sigma value among all peak locations using consistent sample preparation techniques and a limited number of analytic instruments was found to be 0.4. The calibration techniques applied to the instruments to collect these data were within industry standards, but not necessarily as rigorous as the state of the art. Given the facts that sample preparation techniques may vary and other analytic instruments may be used to measure peak locations, a margin of error of about +/−0.5 degrees 2θ may be applied to the data. A standardized sample preparation technique, the use of the same analytic instrument and highly precise calibration of that instrument may increase the repeatability to about +/−0.3 degrees 2θ or less.

Differential Scanning Calorimetry

The DSC instrument used to test the polymorph sample was a TAInstruments® model 2920 (manufactured in 2001), which came equipped with a refrigerated cooling system. The DSC cell/sample chamber was purged with 40 ml/min of ultra-high purity nitrogen gas. The instrument was calibrated with high purity indium. The accuracy of the measured sample temperature with this method is within about +/−1° C., and the heat of fusion can be measured within a relative error of about +/−5%. The sample was placed into a standard aluminum DSC pan with a lid containing two pin holes to allow for pressure release. About 2 mg of sample powder was placed into the bottom of the pan and lightly tapped down to make contact with the pan. The weight of the sample was measured accurately and recorded to a hundredth of a milligram. The instrument used an empty reference pan. The instrument was programmed to equilibrate the sample at about 0° C. for about 1 minute before starting a 2° C./min dynamic heating ramp to about 250° C., with a modulation rate of +/−1° C. every 40 seconds.

The heat flow, which was normalized by a sample weight, was plotted versus the measured sample temperature. The data were reported in units of watts/gram ("W/g"). The plot was made with the endothermic peaks pointing down. The endothermic melt peak was evaluated for extrapolated onset and end (outset) temperatures, peak temperature, and heat of fusion in this analysis.

A DSC profile for Form 1 of Compound 2 is displayed in FIG. 3. FIG. 3 shows that the onset of melt occurs at about 200.6° C. and the melting endotherm is about 206.4° C. The Heat of Fusion is about 52.3 joules/gram ("J/g"). The combination of melt temperature and the Heat of Fusion can be used to distinguish this form from others.

Synthesis of Bisulfate Salt

The preparation of the bisulfate salt, Compound 2 below, is depicted in Scheme I, which employs the following abbreviations: Me is methyl; Et is ethyl; F is fluoro.

Scheme I:
General Synthesis of Compound 2

1

$\xrightarrow{H_2SO_4}$

-continued

2

The preparation of Compound 2 is preferably accomplished in an organic solvent selected from the group consisting of alcohol (e.g., methanol, ethanol, isopropyl alcohol), nitrile (e.g., acetonitrile), ester (e.g., ethyl acetate), ketone (e.g., acetone), ether (e.g., tetrahydrofuran) and mixtures thereof.

Generally, Compound 1 is put in a solvent or solvents mixture and heat (If necessary) is applied thereto until Compound 1 dissolves into solution. The heat applied can vary (e.g., heat sufficient to raise the solvent temperature to about 40–80° C.) depending on the concentration of Compound 1 in the solvent. After the solution forms, the application of heat is continued to maintain the temperature. A solution of sulfuric acid in the same solvent is added slowly. The crystals could come out of solution during the addition of the solution of sulfuric acid. Alternatively, Compound 1 can be contacted with solvents in a suspension or other mixture, without dissolution.

The uses of isopropyl alcohol, acetone, acetonitrile, ethyl acetate, isopropyl acetate and tetrahydrofuran as solvents in the above described process were each found to produce the Form 1 crystalline polymorph.

It is also preferred to seed a saturated solution of Compound 2 in reaction solvent to control the crystallization and minimize and/or prevent encrustation of product on the walls. Encrustation of product will result in yield loss and solvent entrapment in the isolated crystallized product substance. The trapped solvent often cannot be lowered to a preferred level even after prolonged drying. It is preferred that the Compound 2 solution is seeded with a small amount of crystalline Compound 2 (e.g., about 0.1% w/w to about 0.2% w/w) to avoid the potential of product encrustation.

A typical synthesis procedure is as follows. About 5 g of Compound 1 was dissolved in about 25 ml of acetonitrile. The solution was agitated for about 10 minutes and then heated to about 50° C. About 6 ml of 2M sulfuric acid in acetonitrile was added to the heated reaction mixture. Compound 2 precipitated out during the addition of sulfuric acid in acetonitrile. After addition of sulfuric acid solution, the reaction mixture was agitated for 1 hour before cooling to room temperature. The precipitated solid was filtered and washed with about 30 ml of acetonitrile. The wet solid was dried under vacuum at room temperature for 1 hour, and then at 80° C. for about 12 hours to provide about 5 g crystal form of Compound 2. The yield was about 85%. The product was then subjected to PXRD and DSC analyses that resulted in the plots shown in FIGS. 1 and 3, respectively, reflecting the fact that it was the Form 1 polymorph.

Compound Activity, Pharmaceutical Compositions and Methods of Use

In one embodiment, the invention comprises Form 1 of Compound 2, pharmaceutical compositions thereof, a method for making Compound 2, and methods for using Compound 2 or a pharmaceutical composition thereof to treat a variety of disorders, symptoms and diseases. Compound 2 shows activity as a thrombin receptor antagonist, which can be useful in the treatment of diseases associated with thrombosis, atherosclerosis, restenosis, hypertension, angina pectoris, arrhythmia, heart failure, cerebral ischemia, stroke, neurodegenerative diseases and cancer. Thrombin receptor antagonists are also known as protease activated receptor (PAR) antagonists. The class of compounds of which Compound 2 is a member also typically bind to cannabinoid ($CB_2$) receptors and may be useful in the treatment of rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

Formulations and Dosing

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 0.1 to about 95 percent active ingredient. Suitable solid carriers are known in the art, e.g., microcrystalline cellulose, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *The Science and Practice of Pharmacy, 20$^{th}$ Edition*, Lippincott Williams & Wilkins, Baltimore, Md., (2000).

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, Form 1 of Compound 2 is administered orally. Preferably, the pharmaceutical preparation is in a unit dosage form. In such form, the preparation is subdivided into suitably sized unit doses containing appropriate quantities of the active component, e.g., an effective amount to achieve the desired purpose.

The daily dose of Form 1 of Compound 2 for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses.

The amount and frequency of administration of Form 1 of Compound 2 will be regulated according to the judgment of the attending clinician considering such factors as age, condition and size of the patient as well as severity of the symptoms being treated.

Further embodiments of the invention encompass the administration of Form 1 of Compound 2 along with at least one additional therapeutically effective agent. The contemplated additional therapeutically effective agent is one that differs in either atomic make up or arrangement from Compound 2. Therapeutically effective agents that can be used in combination with the novel compounds of this invention include drugs that are known and used in the treatment of inflammation, rheumatism, asthma, glomerulonephritis, osteoporosis, neuropathy and/or malignant tumors, angiogenesis related disorders, cancer, disorders of the liver, kidney and lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases, conditions, or injuries, radiation fibrosis, endothelial dysfunction, periodontal diseases and wounds. Further examples of therapeutically effective agents which may be administered in combination with Compound 2 include resistance factors for tumor cells towards chemotherapy and proliferation inhibitors of smooth muscle cells, endothelial cells, fibroblasts, kidney cells, osteosarcoma cells, muscle cells, cancer cells and/or glial cells. The therapeutically effective agents may be cardiovascular agents.

Cardiovascular agents that can be used in combination with the novel compounds of this invention include drugs that have anti-thrombotic, anti-platelet aggregation, antiatherosclerotic, antirestenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartran, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anticoagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Preferred types of drugs for use in combination with Form 1 of Compound 2 are thromboxane A2 biosynthesis inhibitors, cyclooxygenase inhibitors and ADP antagonists. Especially preferred for use in the combinations are aspirin and clopidogrel bisulfate.

Further embodiments of the invention encompass the administration of Form 1 of Compound 2 along with more than one additional therapeutically effective agent. In these embodiments, the additional therapeutically effective agent may or may not be commonly used in the treatment of the same condition. For example, Form 1 of Compound 2 may be administered along with two cardiovascular agents. Alternatively, Form 1 of Compound 2 may be administered along with a cardiovascular agent and a therapeutically effective agent useful in the treatment of inflammation.

When the invention comprises a combination of Form 1 of Compound 2 and one or more other therapeutically effective agents, the two or more active components may be co-administered simultaneously or sequentially, or a single pharmaceutical composition comprising Form 1 of Compound 2 and the other therapeutically effective agent(s) in a pharmaceutically acceptable carrier can be administered. The components of the combination can be administered individually or together in any conventional dosage form such as capsule, tablet, powder, cachet, suspension, solution, suppository, nasal spray, etc. The dosage of the other therapeutically active agent(s) can be determined from published material, and may range from 1 to 1000 mg per dose.

In this specification, the term "one or more additional cardiovascular agents" means that one to three additional drugs may be administered in combination with Form 1 of Compound 2; preferably, one additional compound is administered in combination with Form 1 of Compound 2. The additional cardiovascular agents can be administered sequentially or simultaneously with reference to Form 1 of Compound 2.

The rate of systemic delivery can be satisfactorily controlled by one skilled in the art, by manipulating any one or more of the following:

(a) the active ingredient(s) proper;
(b) the pharmaceutically-acceptable excipient(s) or carrier(s), so long as the variants do not interfere in the activity of the particular active ingredient(s) selected;
(c) the type of excipient(s) or carrier(s), and the concomitant desirable thickness and permeability (swelling properties) of the excipient(s) or carrier(s);
(d) the time-dependent conditions of the excipient(s) or carrier(s);
(e) the particle size of the active ingredient; and
(f) the pH-dependent conditions of the excipient(s) or carrier(s).

Pharmaceutically-acceptable excipients or carriers comprise flavoring agents, pharmaceutical-grade dyes or pigments, solvents, co-solvents, buffer systems, surfactants, preservatives, sweetener agents, viscosity agents, fillers, lubricants, glidants, disintegrants, binders and resins.

Conventional flavoring agents can be used, such as those described in *Remington's Pharmaceutical Sciences*, 18th Ed., Mack Publishing Co., 1288–1300 (1990), which is incorporated by reference herein. The pharmaceutical compositions of the invention generally comprise from 0% to about 2% of flavoring agent(s).

Conventional dyes and/or pigments can also be used, such as those described in the *Handbook of Pharmaceutical Excipients*, by the American Pharmaceutical Association & the Pharmaceutical Society of Great Britain, 81–90 (1986), which is incorporated by reference herein. The pharmaceutical compositions of the invention generally comprise from 0% to about 2% of dye(s) and/or pigment(s).

The pharmaceutical compositions of the invention generally comprise from about 0.1% to about 99.9% of solvent(s). A preferred solvent is water. Preferred co-solvents comprise ethanol, glycerin, propylene glycol, polyethylene glycol, and the like. The pharmaceutical compositions of the invention can comprise from 0% to about 50% of co-solvent(s).

Preferred buffer systems comprise acetic, boric, carbonic, phosphoric, succinic, malic, tartaric, citric, acetic, benzoic, lactic, glyceric, gluconic, glutaric and glutamic acids and their sodium, potassium and ammonium salts. Particularly preferred buffers are phosphoric, tartaric, citric and acetic acids and salts thereof. The pharmaceutical compositions of the invention generally comprise from 0% to about 5% of buffer(s).

Preferred surfactants comprise polyoxyethylene sorbitan fatty acid esters, polyoxyethylene monoalkyl ethers, sucrose monoesters and lanolin esters and ethers, alkyl sulfate salts and sodium, potassium and ammonium salts of fatty acids. The pharmaceutical compositions of the invention generally comprise from 0% to about 2% of surfactant(s).

Preferred preservatives comprise phenol, alkyl esters of parahydroxybenzoic acid, o-phenylphenol benzoic acid and salts thereof, boric acid and salts thereof, sorbic acid and salts thereof, chlorobutanol, benzyl alcohol, thimerosal, phenylmercuric acetate and nitrate, nitromersol, benzalkonium chloride, cetylpyridinium chloride, methyl paraben and propyl paraben. Particularly preferred preservatives are the salts of benzoic acid, cetylpyridinium chloride, methyl paraben and propyl paraben. The pharmaceutical compositions of the invention generally comprise from 0% to about 2% of preservative(s).

Preferred sweeteners comprise sucrose, glucose, saccharin, sorbitol, mannitol and aspartame. Particularly preferred sweeteners are sucrose and saccharin. Pharmaceutical compositions of the invention generally comprise from 0% to about 5% of sweetener(s).

Preferred viscosity agents comprise methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred viscosity agents are methylcellulose, carbomer, xanthan gum, guar gum, povidone, sodium carboxymethylcellulose, and magnesium aluminum silicate. Pharmaceutical compositions of the invention generally comprise from 0% to about 5% of viscosity agent(s).

Preferred fillers comprise lactose, mannitol, sorbitol, tribasic calcium phosphate, diabasic calcium phosphate, compressible sugar, starch, calcium sulfate, dextro and microcrystalline cellulose. Pharmaceutical compositions of the invention generally comprise from 0% to about 90% of filler(s).

Preferred lubricants/glidants comprise magnesium stearate, stearic acid and talc. Pharmaceutical compositions of the invention generally comprise from 0% to 7%, preferably, from about 1% to about 5%, of lubricant(s)/glidant(s).

Preferred disintegrants comprise starch, sodium starch glycolate, crospovidone and croscarmelose sodium and microcrystalline cellulose. Pharmaceutical compositions of the invention generally comprise from 0% to about 20%, preferably, from about 4% to about 15%, of disintegrant(s).

Preferred binders comprise acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. Pharmaceutical compositions of the invention generally comprise from 0% to about 12%, preferably, from about 1% to about 10%, of binder(s).

Additional agents known to a skilled formulator may be combined with the inventive compounds to create a single dosage form. Alternatively, additional agents may be separately administered to a mammal as part of a multiple dosage form.

A pharmaceutical composition typically comprises from about 0.1% to about 99.9% (by weight or volume, preferably, w/w) of active ingredient (Form 1 of Compound 2), preferably, from about 5% to about 95%, more preferably, from about 20% to about 80%. For preparing pharmaceutical compositions comprising Form 1 of Compound 2, inert, pharmaceutically acceptable excipients or carriers can be either solid or liquid. Solid form preparations comprise powders, tablets, dispersible granules, capsules, cachets and suppositories. Suitable solid excipients or carriers are known in the art, for example, magnesium carbonate, magnesium stearate, talc, sugar and lactose. Tablets, powders, cachets and capsules can be used as solid dosage forms suitable for oral administration. Examples of pharmaceutically-acceptable excipients or carriers and methods of manufacture for various compositions may be found in *Remington's Pharmaceutical Sciences*, 18$^{th}$ Ed., Mack Publishing Co. (1990), which is incorporated in its entirety by reference herein.

Liquid form preparations comprise solutions, suspensions and emulsions. Common liquid form preparations comprise water and water-propylene glycol solutions for parenteral injection or addition of sweeteners and opacifiers for oral solutions, suspensions and emulsions. Liquid form preparations may also comprise solutions for intranasal administration.

The quantity of Form 1 of Compound 2 in a unit dose of preparation may be varied or adjusted from about 0.01 mg to about 4,000 mg, preferably, from about 0.02 mg to about 2,000 mg, more preferably, from about 0.03 mg to about 1,000 mg, even more preferably, from about 0.04 mg to about 500 mg, and most preferably, from about 0.05 mg to about 250 mg, according to the particular application. A typical recommended daily dosage regimen for oral administration can range from about 0.02 mg to about 2,000 mg/day, in two to four divided doses. For convenience, the total daily dosage may be divided and administered in portions during the day as required. Typically, pharmaceutical compositions of the invention will be administered from about 1 time per day to about 5 times per day, or alternatively, as a continuous infusion. Such administration can be used as a chronic or acute therapy.

The pharmaceutically-acceptable excipients or carriers employed in conjunction with the compounds of the present invention are used at a concentration sufficient to provide a practical size to dosage relationship. The pharmaceutically-acceptable excipients or carriers, in total, can comprise from about 0.1% to about 99.9% (by weight or volume, preferably, by w/w) of the pharmaceutical compositions of the invention, preferably, from about 5% to about 95% by weight, more preferably, from about 20% to about 80% by weight.

Upon improvement of a patient's condition, a maintenance dose of a compound, composition or combination of the invention can be administered, if desired or warranted. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art. The amount and frequency of the administration of Form 1 of Compound 2, or the pharmaceutical compositions thereof, may be regulated according to the judgment of the attending clinician, based on the factors recited above. As a skilled artisan will appreciate, lower or higher doses than those recited above may be required.

For instance, it is often the case that a proper dosage level is based on the weight of the patient. For example, dosage levels of between about 0.01 mg/kg and about 100 mg/kg of body weight per day, preferably, between about 0.5 mg/kg and about 75 mg/kg of body weight per day, and more preferably, between about 1 mg/kg and about 50 mg/kg of body weight per day, of the inventive compound(s), and compositions described herein, are therapeutically useful for the treatment of a variety of biological disorders, particularly, thrombosis and other cardiovascular conditions. Between two patients of differing weights, a higher dosage will be used for the heavier patient, all other things being equal.

Polymorph Purity

Preferably, the crystalline polymorph Form 1 of Compound 2 is substantially free of chemical impurities (e.g., by-products generated during the preparation of Compound 2) and of other polymorphic crystalline forms. "Substantially free" of chemical impurities for the purposes of this invention means less than or equal to about 5% w/w of chemical impurities, preferably, less than or equal to about 3% w/w of chemical impurities, more preferably, less than or equal to about 2% w/w of chemical impurities, and even more preferably, less than or equal to about 1% w/w of chemical impurities. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan. Purified forms of the crystalline polymorph Form 1 of Compound 2 are substantially free of chemical impurities.

Other than as shown in the operating example or as otherwise indicated, all numbers used in the specification and claims expressing quantities of ingredients, reaction conditions, and so forth, are understood as being modified in all instances by the term "about." The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A crystalline polymorph Form 1 of Compound 2 of the formula:

Compound 2 that exhibits a powder x-ray diffraction pattern having characteristic peak locations of 11.2, 16.4, 19.2 and 21.0 degrees 2θ.

2. The crystalline polymorph of Compound 2 of claim 1 that exhibits a powder x-ray diffraction pattern having characteristic peak locations of 9.9, 11.2, 16.4, 19.2, 21.0, 22.1, 23.7 and 26.7 degrees 2θ.

3. The crystalline polymorph of Compound 2 of claim 1 that exhibits a powder x-ray diffraction pattern having characteristic peak locations of 9.9, 11.2, 12.6, 14.5, 16.4, 19.2, 21.0, 22.1, 23.7, 26.7, 28.2 and 30.8 degrees 2θ.

4. The crystalline polymorph of Compound 2 of claim 1 that exhibits a powder x-ray diffraction pattern substantially the same as the powder x-ray diffraction pattern shown in FIG 1.

5. A crystalline polymorph Form 1 of Compound 2 of the formula:

Compound 2 that exhibits a differential scanning calorimetry pattern substantially the same as the differential scanning calorimetry pattern shown in FIG. 3.

6. A pharmaceutical composition comprising the crystalline polymorph Form 1 of Compound 2 according to claim 1, and at least one excipient or carrier.

7. A purified form of the crystalline polymorph Form 1 of Compound 2 of claim 1.

* * * * *